United States Patent [19]

Eldor

[11] Patent Number: 5,800,407
[45] Date of Patent: Sep. 1, 1998

[54] MULTIPLE HOLE EPIDURAL CATHETER

[76] Inventor: Joseph Eldor, 4 Hanayadot Street, Pisgat Zeev, Jerusalem 97536, Israel

[21] Appl. No.: 576,014

[22] Filed: Dec. 21, 1995

[51] Int. Cl.$^6$ ................................................. A61M 25/00
[52] U.S. Cl. ........................................... 604/264; 604/280
[58] Field of Search ...................................... 604/264, 272, 604/280, 51, 118, 43, 27, 21

[56] References Cited

U.S. PATENT DOCUMENTS

| | | | |
|---|---|---|---|
| 4,402,684 | 9/1983 | Jessup | 604/264 |
| 4,583,968 | 4/1986 | Mahurkar | 604/280 X |
| 4,682,978 | 7/1987 | Martin | 604/283 X |
| 4,801,297 | 1/1989 | Mueller | 604/280 |
| 5,061,257 | 10/1991 | Martinez et al. | |
| 5,069,673 | 12/1991 | Schwab | |
| 5,106,376 | 4/1992 | Mononen et al. | 604/51 X |
| 5,300,022 | 4/1994 | Klapper et al. | 604/43 X |
| 5,344,412 | 9/1994 | Wendell et al. | 604/280 |
| 5,360,397 | 11/1994 | Pinchuk | 604/27 |
| 5,364,344 | 11/1994 | Beattie et al. | 604/280 X |
| 5,601,539 | 2/1997 | Corso, Jr. | 604/264 X |

FOREIGN PATENT DOCUMENTS

| | | | |
|---|---|---|---|
| 1142769 | 9/1957 | France | 604/272 |

OTHER PUBLICATIONS

Durow, "The Occurrence of Unblocked Segments During Continuous Lumber Epidural Analgesia for Pain Relief in Labour", *Br. J. Anaesth*, vol. 43, pp. 1172–1174 (1971).
Scott et al. "Insertion of Epidural Catheters" *Anaesthesia*, vol. 38, pp. 1108–1109 (1983).
Kumar et al., "Excessive Dose Requirements of Local Anaesthesia, How Far Should an Epidural Catheter be Inserted?" *Anaesthesia*, vol. 40, pp. 1100–1102 (1985).
Beck et al., "Epidural Catheters of the Multi–Orifice Type: Dangers and Implecations", *Acta Anaesthesiol Scand.*, vol. 30, pp. 549–555 (1986).
Ward et al., "A Hazard of Double–Orifice Epidural Catheters", *Anesthsiology* vol. 48, pp. 362–364 (1986).
Finucaine, "Double–Orifice Epidural Catheters Safe?", *Anesthesiology*, vol. 59, p. 168 (1979).
Finucaine, "Safety of Double–Orifice Epidural Catheters", *Can. Anaesth. Soc. J.*, vol. 26, p. 146 (1979).
Power et al., "Differential Flow from Multihole Epidural Catheters", *Anaesthesia*, vol. 43, pp. 876–878 (1988).
Ward et al., "Double–Orifice Epidural Catheters Safe?—Reply", *Anesthesiology*, vol. 50, p. 168 (1979).
Michael et al., "A Comparison Between Open–End (Single Hole) and Closed–End (Three Lateral Holes) Epidural Catheters", *Anaesthesia*, vol. 44, pp. 578–580 (1989).
Collier et al., "A New Epidural Catheter: Closer Eyes for Safety?", *Anaesthesia*, vol. 48, pp. 803–806 (1993).
Collier et al., "Epidural Catheter for Obstetrics: Terminal Hole or Lateral Eyes?", *Reg. Anesth.*, vol. 19, pp. 378–385 (1994).
Curbelo, "Continuous Peridural Segmental Anesthesia by Means of an Ureteral Catheter", *Anesth. Analg.*, vol. 28, pp. 13–23 (1949).
Lee, "A New Catheter for Continuous Extradural Analgesia", *Anaesthsia*, vol. 17, pp. 248–250 (1962).
Skinner, "A New Epidural Cannula", *Can. Anaesth. Soc. J.*, vol. 13, pp. 622–623 (1966).
Crawford, "Principles and Practice of Obstetric Anaesthesia", Blackwell Scientific Publications, 4th Ed pp. 169–172 (1978).

*Primary Examiner*—John D. Yasko
*Attorney, Agent, or Firm*—Reising, Ethington, Learman & McCulloch

[57] ABSTRACT

An epidural catheter which combines the benefits of the open-end and closed-end three lateral holes type catheters. The epidural catheter of the present invention is designed to include an end hole and a plurality of lateral holes epidural catheter. The combined end and multiple lateral holed epidural catheter of the present invention includes seven holes within a 1.5 cm head. The holes are positioned along the head such that one hole is provided at the tip, three lateral holes are circumferentially arranged about the head at approximately 1 mm from each other, and three additional holes are axially displaced from one another by approximately 4 mm. All the holes are within the 1.5 cm from the tip. The radius of each of the lateral holes is the same, thus, the anesthetic solution stream is the same from each hole.

17 Claims, 2 Drawing Sheets

MULTIPLE HOLE EPIDURAL CATHETER

CROSS-REFERENCE OF RELATED APPLICATIONS

The present invention is based upon Israel Patent Application No. 112418 filed on Jan. 23, 1995, the disclosure of which is incorporated herein by reference in its entirety.

BACKGROUND OF THE INVENTION

1. Field of the Invention

The present invention relates to a device for continuous epidural analgesia. In particular, the present invention relates to a combined end and multiple lateral holed epidural catheter (CEMLH).

2. Discussion of the Background Information

Continuous epidural analgesia is the most successful method for relief of labor pain, but can, at times, be difficult to perform. The failure rate, even in skilled hands, may be as high as 8%. This failure rate may be attributable to poor technique or abnormal placement of an epidural catheter, even when the catheter is passed through a successfully placed epidural needle. Abnormal catheter placement may include blocked, kinked or bent catheters, deviation through an intervertebral foramen, and passage into an epidural vein or a subdural or subarachnoid space.

Epidural catheter design may influence the successful outcome of epidural analgesia. There are two main types of epidural catheter in common use in obstetric practice: the single or end-holed catheter and the closed-end, multi- or side-holed catheter. The closed-end catheter, which includes, for example, three lateral holes, is recognized as presenting potential problems with multicompartmental placement, i.e., different holes lying within different anatomical spaces. While open-end single-hole catheters do not present the above complication, open-end catheters are more likely to become blocked, particularly by clotted blood.

Both designs provide certain benefits for the user. The single-holed catheter is believed safer than the closed-end design because malpositioning of the catheter may be more readily discovered. However, closed-end multi-holed catheters are generally believed to be less likely to obstruct the flow of anesthetic, allowing wider distribution of local anesthetic in the epidural space. Thus, even if partially malpositioned within the subarachnoid space or extradural vein, most of the local anesthetic enters the epidural space. However, using the multi-holed catheter makes the discovery of catheter malpositioning of utmost importance. Because of the multi-holed design, a malpositioned catheter, e.g., in which the distal hole is positioned within the subarachnoid space and the two proximal holes are positioned within the epidural space, may not be discovered until top-up, thus making it potentially hazardous.

When open-end and closed-end epidural catheters are compared, as in, e.g., MICHAEL et al., "A Comparison Between Open-End (Single Hole) and Closed-End (Three Lateral Holes) Epidural Catheters", *Anaesthesia*, vol. 41, pp. 578–80 (1989), one generally finds that the open-end catheter results in an unacceptably high incidence of blockage. Collier and Gatt, in "A New Epidural Catheter: Closer Eyes for Safety?", *Anaesthesia*, vol. 48, pp. 803–06 (1993), found that the incidence of unsatisfactory blocks in the terminal hole catheter to be "unacceptably high" (32%) when compared with the three lateral hole catheter (12%).

Most of the epidural catheters used in the U.S.A. are of the single terminal hole, while most of those used in the UK are of the three lateral holes with a blunted end.

Curbelo, "Continuous Peridural Segmental Anesthesia by Means of an Ureteral Catheter", *Anesthesia Analg.*, vol. 28, pp 13–23 (1949), indicates that the epidural catheter was first used for epidural anesthesia in 1947. The catheter was of the end hole type. In 1962, an epidural catheter was introduced by Lee, "A New Catheter for Continuous Extradural Analgesia," *Anesthesia*, vol. 17, pp. 248–250 (1962), in which the tip was smooth, to facilitate insertion, and a solution was output to the insertion space from a small opening approximately 1 cm from the tip. Prior to the prepackaged epidural catheter of Lee, anesthetists had employed polyvinyl chloride tubing and nylon infant's ureteric catheters and cut it by themselves. In 1966, Skinner, "A New Epidural Cannula," *Can. Anaesth. Soc. J.*, vol. 13 pp. 622–23 (1966), introduced another epidural catheter with a blunt tip of the cannula with a hole in the end. A second hole was positioned 3 mm from the distal end. This design virtually rendered kinking impossible under the stresses involved with normal use. Recently, an epidural catheter was described. Designed by Portex, with a closed end and three lateral holes spaced at approximately 2, 3 and 4 mm from the smooth closed tip, this design suggests that the close spacings of the holes will eliminate the complication of multi-compartment block, as seen with earlier multi-hole epidural catheters.

SUMMARY OF THE INVENTION

It is one of the objects of the present invention to overcome the limitations and drawbacks of the prior art applicators for continuous epidural analgesia, and to provide a device that considerably simplifies the procedure. Accordingly, the present invention achieves this object by providing an end hole and a plurality of lateral holes arranged along a proximal end of the epidural catheter.

It is another aspect of the present invention to provide an epidural catheter in which the end hole recognizes an intravascular or intrathecal insertion of the epidural catheter tip, which a blunted, closed-end tip cannot.

Yet another aspect of the present invention is to provide an epidural catheter in which a plurality of lateral holes are circumferentially spaced about the tip to allow anesthetic solution injection into the epidural space even when the end hole is obstructed by a blood clot or tissue. The particular design of the present invention also gives a better distribution of anesthetic solution thus, avoiding a partial block.

Accordingly, one aspect of the present invention is to provide an epidural catheter which combines the benefits of the open-end and closed-end three lateral holes type catheters. The epidural catheter of the present invention is designed to include an end hole and a plurality of lateral holes.

It is another aspect of the present invention to provide a CEMLH epidural catheter that includes seven holes within a 1.5 cm head. The holes are positioned along the head such that one hole is provided at the tip, three lateral holes are circumferentially arranged about the head at approximately 1 mm from each other, and three additional holes are axially displaced from one another by approximately 4 mm. All the holes are within 1.5 cm from the tip. The radius of each of the lateral holes is the same, thus, the anesthetic solution stream from each hole is the same.

Accordingly, it is an aspect of the present invention to provide a device for continuous epidural analgesia that includes a first portion including a first plurality of holes, a second portion including a second plurality of holes, and one of the first plurality of holes being positioned at a tip of the first portion.

It is another aspect of the present invention that a remainder of the first plurality of holes are spaced circumferentially and axially along the first portion.

It is yet another aspect of the present invention that the second plurality of holes are spaced circumferentially and axially along the second portion.

It is still another aspect of the present invention that the remainder of the first plurality of holes are equidistantly spaced circumferentially around a periphery of the catheter and equidistantly spaced axially along a length of the first portion, and the second plurality of holes are equidistantly spaced circumferentially around the periphery of the catheter and equidistantly spaced axially along a length of the second portion.

It is another aspect of the present invention that the length of the first portion is 3 mm long and the length of the second portion is 1.2 cm long.

It is another aspect of the present invention that a first of the second plurality of holes is positioned 7 mm from the tip.

BRIEF DESCRIPTION OF THE DRAWINGS

The present invention is further described in the detailed description which follows, in reference to the noted plurality of drawings by way of non-limiting examples of preferred embodiments of the present invention, in which like reference numerals represent similar parts throughout the several views of the drawings, and wherein.

DETAILED DESCRIPTION OF THE PREFERRED EMBODIMENTS

The particulars shown herein are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.

Figure 1:
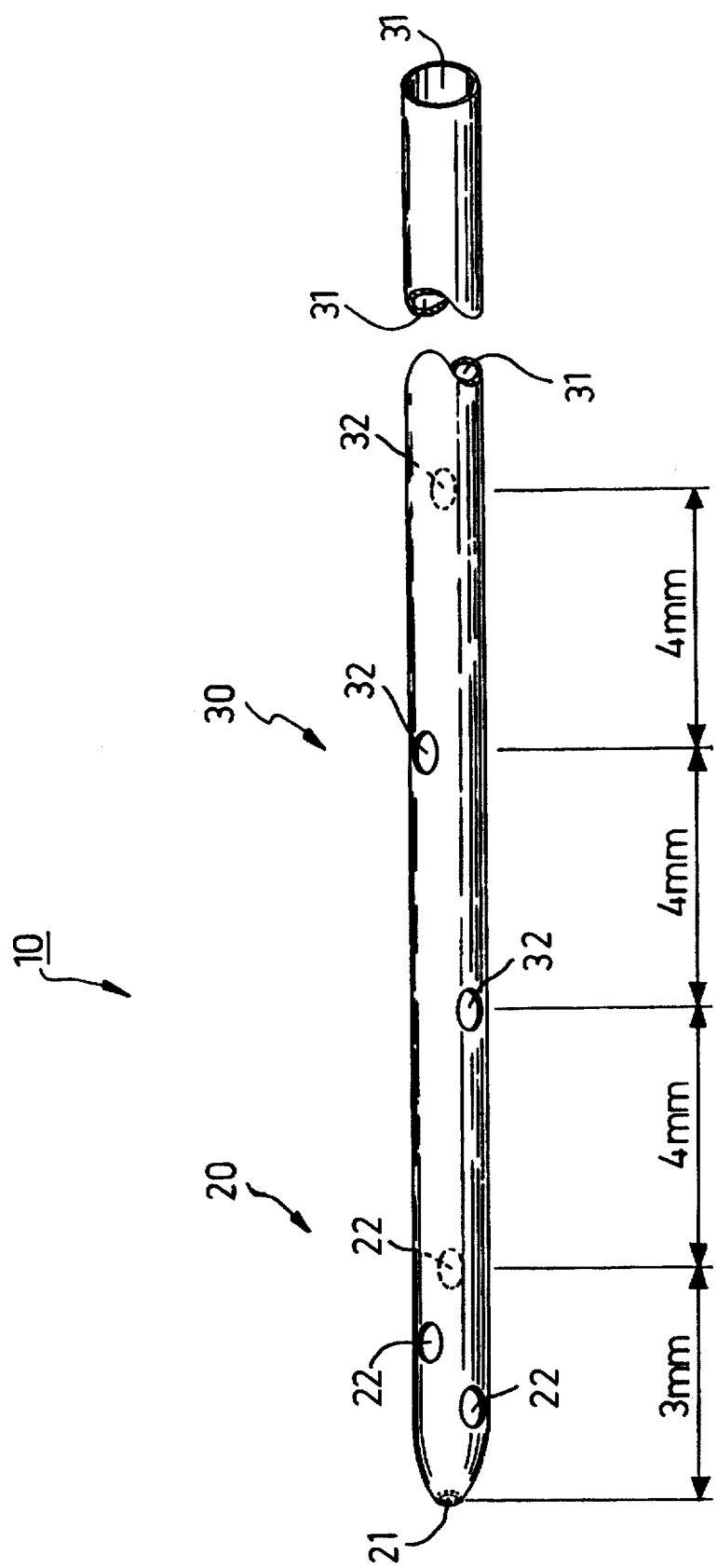
FIG. 1 shows a head of a combined end-multiple lateral holed epidural catheter according to the present invention.

FIG. 1 shows an insertion end of a combined end and multiple lateral holed (CEMLH) epidural catheter 10 for providing continuous epidural analgesia according to the present invention. The insertion end comprises a first portion 20 and a second portion 30 and may measure, for example, approximately 1.5 cm. The insertion end includes an end hole 21 located at the tip of the first portion 20.

According to the present invention, each of the lateral holes 22 and 32 may be preferably formed of equal size, for example, approximately 0.014 in. in diameter, to regulate the streams of epidural analgesic flowing therethrough. End hole 21 may be formed to be, for example, approximately 0.010 in. in diameter. It should be noted that the holes may slightly vary in size from each other in order to achieve equal analgesic streams flowing from the catheter.

As shown, first portion 20 and second portion 30 may be only a part of a much longer catheter tube 10, e.g., approximately 36 in. The catheter tube 10 may have an inside diameter of, e.g., approximately 0.034 in., forming a single passageway 31 and a wall thickness of, e.g., approximately 0.010 in.

Figure 2:
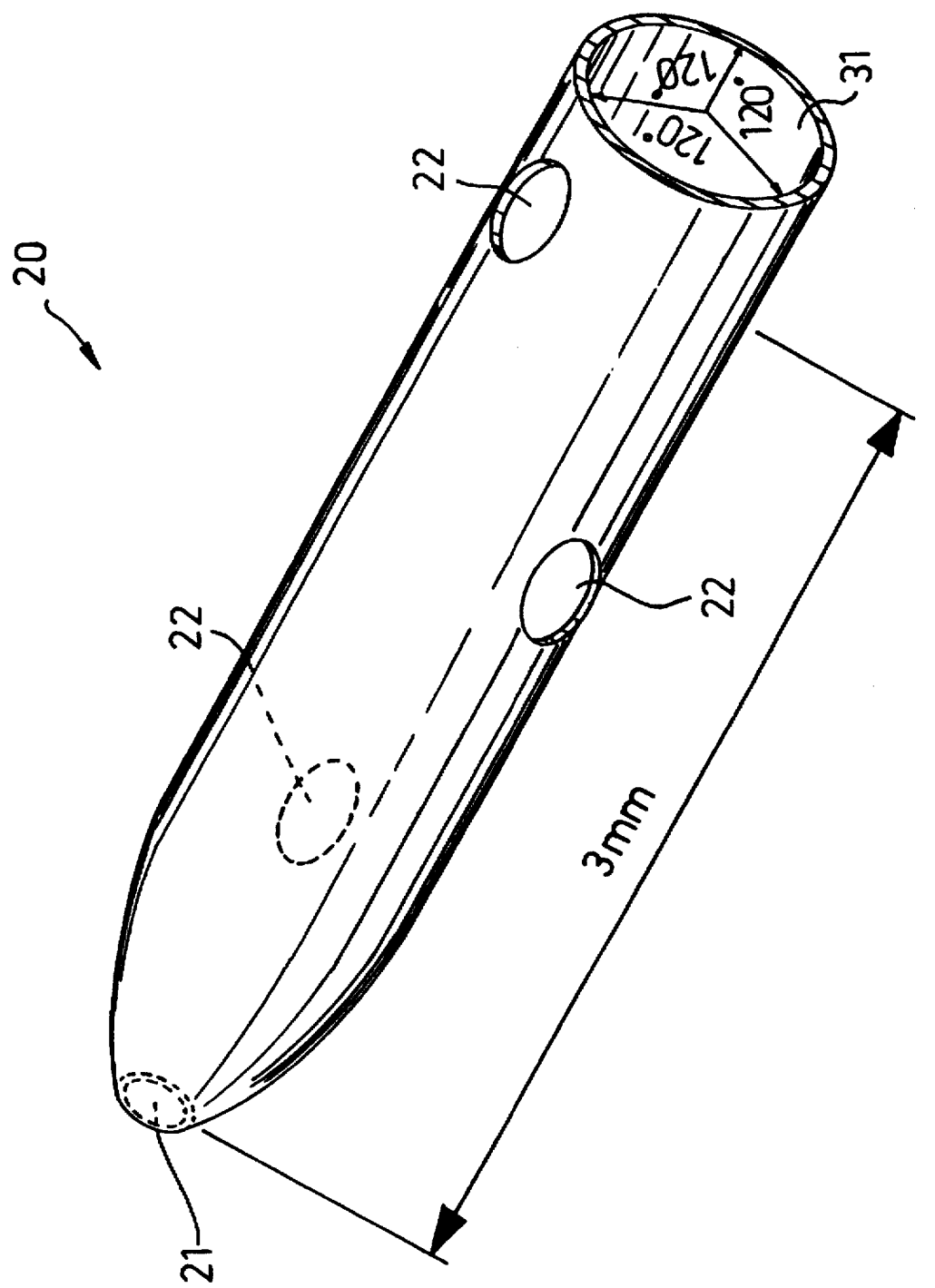
FIG. 2 shows the tip of the head depicted in FIG. 1 showing the end hole and three lateral holes at 1, 2 and 3 mm from the tip.

FIG. 2 shows an enlarged view of the first portion 20 of the epidural catheter 10. "The first portion 20 includes the tip which is tapered by a converging wall of the catheter and the end hole 21 is at the end of the tapered tip." In addition to the end hole 21, the first portion 20 is provided with a plurality of lateral holes 22, e.g., three. The lateral holes are preferably circumferentially and axially arranged around the first portion 20. In the embodiment shown, the three lateral holes 22 are circumferentially positioned 120° apart, i.e., 360°/n, and axially disposed 1 mm apart, i.e., 3 mm/n, where "n" represents the number of lateral holes 22 disposed within the first portion 20.

The second portion 30 may be, for example, 1.2 cm in length, and is provided with a plurality of lateral holes 32, e.g., three. As with the first portion 20, the lateral holes 32 of the second portion 30 are preferably circumferentially and axially arranged around the second portion 30. In the embodiment shown, the three lateral holes 32 are circumferentially positioned 120° apart, i.e., 360/x, and axially disposed 4 mm apart, i.e., 1.2 cm/x, where "x" represents the number of lateral holes 32 disposed within the second portion 30.

The CEMLH epidural catheter 10 of the present invention may be formed of, e.g., nylon or any other suitable material known to those ordinarily skilled in the art, and may be used in the same manner as conventional epidural catheters. Further, epidural catheter 10 may additionally be provided with indicia, e.g., stripes, observable by the user to determine depth of penetration, etc. The stripes may be encapsulated within catheter 10 so as not to restrict movement and may be made of any suitable material, e.g., nylon with barium sulfate and black colorant (for visibility).

Further, the catheter 10 of the present invention does not suffer the several drawbacks noted above. Because the epidural catheter 10 of the present invention includes, for example, six lateral holes 22, 32 within, for example, approximately 1.5 cm of the end hole 21, the epidural analgesic streaming from each of the holes diverted from the passageway 31 is substantially equal.

However, while the embodiment shown in FIG. 1 shows six lateral holes 22, 32 located in the insertion end of the catheter 10, the present invention should not be construed as limited by any specific number of lateral holes, because any number of holes may be employed in accordance with the present invention as long as the injected streams of analgesic are not adversely affected.

The circumferential arrangement of the holes about the catheter 10 enables epidural analgesic to flow through the catheter, even when the end hole is blocked or obstructed by a blood clot or tissue.

The catheter 10, according to the present invention, may recognize, via the end hole 21, an intravascular or an intrathecal insertion of the catheter.

It is noted that the foregoing examples have been provided merely for the purpose of explanation and are in no way to be construed as limiting of the present invention. While the invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the invention in its aspects. Although the invention has been described herein with reference to particular means, materials and embodiments, the invention is not intended to be limited to the particulars disclosed herein; rather, the invention extends to all functionally equivalent structures, methods and uses, such as are within the scope of the appended claims.

What is claimed is:

1. A device for continuous epidural analgesia comprising:

an epidural catheter having a single passageway with an end hole and a plurality of side holes, wherein said end hole is smaller in diameter than said side holes for providing flow of epidural analgesic through the passage way and out through said end hole and side holes.

2. The device as claimed in claim 1, wherein said plurality of side holes are formed of a same radius.

3. The device as claimed in claim 1, wherein said plurality of side holes are circumferentially arranged around said epidural catheter.

4. The device as claimed in claim 1, wherein said plurality of side holes includes three lateral holes axially arranged 1 mm apart, and a first of said three lateral holes being axially positioned 1 mm from said end hole.

5. The device as claimed in claim 1, wherein said plurality of side holes includes three lateral holes axially arranged 4 mm apart, and a first of said three lateral holes being positioned 7 mm from said end hole.

6. An epidural catheter comprising:

a tubular member with a single passageway through its interior and having a distal tip;

a first portion of said tubular member including a first plurality of holes;

a second portion of said tubular member including a second plurality of holes; and one of said first plurality of holes positioned at a tip of said first portion, said one of said first plurality of holes being smaller in diameter than the remainder of said first plurality of holes and said second plurality of holes for providing flow of epidural analgesic through the single passageway and out through said first and second plurality of holes.

7. The epidural catheter according to claim 6, a remainder of said first plurality of holes spaced circumferentially and axially along said first portion.

8. The epidural catheter according to claim 7, said second plurality of holes spaced circumferentially and axially along said second portion.

9. The epidural catheter according to claim 8, a remainder of said first plurality of holes are equidistantly spaced circumferentially around a periphery of said catheter and equidistantly spaced axially along a length of said first portion; and said second plurality of holes are equidistantly spaced circumferentially around said periphery of said catheter and equidistantly spaced axially along a length of said second portion.

10. The epidural catheter according to claim 9, said length of said first portion being 3 mm long and said length of said second portion being 1.2 cm long.

11. The epidural catheter according to claim 9, wherein a first of said second plurality of holes is positioned 7 mm from said tip.

12. The epidural catheter according to claim 6, said one of said first plurality of holes being smaller in diameter than said remainer of said first plurality of holes and said second plurality of holes.

13. The epidural catheter according to claim 6, said remainder of said first plurality of holes and said second plurality of holes being of substantially equal diameter.

14. The epidural catheter according to claim 13, said diameter being approximately 0.014 inches.

15. The epidural catheter according to claim 6, wherein a diameter of said one of said first plurality of holes being approximately 0.010 inches.

16. The epidural catheter according to claim 6, wherein said catheter includes a outside diameter of approximately 0.034 inches and a wall thickness of approximately 0.010 inches.

17. The epidural catheter according to claim 6, said catheter further comprising indicia for determining a depth of penetration.

* * * * *

UNITED STATES PATENT AND TRADEMARK OFFICE
CERTIFICATE OF CORRECTION

PATENT NO. : 5,800,407
DATED : September 1, 1998
INVENTOR(S) : Joseph Eldor

It is certified that error appears in the above-identified patent and that said Letters Patent is hereby corrected as shown below:

In the Claims:

Please add claims 18 and 19

18. A device as claimed in claim 1 further comprising said catheter having a tapered end with a converging wall and the end hole being positioned at the tip of the tapered end.

19. The epdural catheter as defined in claim 6 further comprising said tip being tapered and said one of the said first plurality of holes being positioned at the end of the tapered tip.

Signed and Sealed this

Fourth Day of January, 2000

Attest:

Attesting Officer

*Acting Commissioner of Patents and Trademarks*